(12) United States Patent
Bürli et al.

(10) Patent No.: US 12,721,944 B2
(45) Date of Patent: Sep. 1, 2026

(54) DRUG DELIVERY DEVICE

(71) Applicant: SENSILE MEDICAL AG, Olten (CH)

(72) Inventors: Fabian Bürli, Stüsslingen (CH); Pascal Lagorgette, Bienne (CH)

(73) Assignee: SENSILE MEDICAL AG, Olten (CH)

( * ) Notice: Subject to any disclaimer, the term of this patent is extended or adjusted under 35 U.S.C. 154(b) by 432 days.

(21) Appl. No.: 18/489,887

(22) Filed: Oct. 19, 2023

(65) Prior Publication Data

US 2024/0131254 A1 Apr. 25, 2024
US 2024/0226425 A9 Jul. 11, 2024

(30) Foreign Application Priority Data

Oct. 21, 2022 (EP) .................................... 22203156

(51) Int. Cl.
*A61M 5/142* (2006.01)
*A61M 5/158* (2006.01)

(52) U.S. Cl.
CPC ........ *A61M 5/14248* (2013.01); *A61M 5/158* (2013.01); *A61M 2005/14256* (2013.01);
(Continued)

(58) Field of Classification Search
CPC .......... A61M 5/14248; A61M 5/14252; A61M 5/14256; A61M 5/1452; A61M 5/158;
(Continued)

(56) References Cited

U.S. PATENT DOCUMENTS 7,726,955 B2 6/2010 Ryser et al.
8,282,366 B2 10/2012 Hilber et al.
(Continued)

FOREIGN PATENT DOCUMENTS

EP 4 035 707 8/2022
WO WO 2007/074363 7/2007
(Continued)

OTHER PUBLICATIONS

Extended European Search Report for Application No. EP 22203156.9, Mar. 15, 2023, pp. 1-9.

*Primary Examiner* — Andrew M Gilbert
(74) *Attorney, Agent, or Firm* — SALIWANCHIK, LLOYD & EISENSCHENK

(57) ABSTRACT

A drug delivery device (1), including a delivery unit (3) comprising a subcutaneous delivery system including a needle support (10), an injection needle (9) mounted on the needle support, and an injection needle actuation mechanism configured to engage and slidably move the needle support from a retracted position where the injection needle is within a housing (2) of the drug delivery device to an extended delivery position where the injection needle projects through a skin contact wall of the housing. The needle actuation mechanism comprises a slider-crank linkage mechanism (11) comprising a crank rod (13) pivotally connected to the housing, a connecting rod (14) pivotally connected to the crank rod and pivotally connected to the slidable needle support (10), and a spring (12) biasing the slider-crank linkage mechanism from a first retracted position prior to use where the needle is fully inserted within the housing towards an extended position for drug administration and further to a second retracted position after use.

19 Claims, 5 Drawing Sheets

(52) U.S. Cl.
CPC ............... *A61M 2005/1585* (2013.01); *A61M 2202/0007* (2013.01); *A61M 2202/04* (2013.01); *A61M 2205/0216* (2013.01); *A61M 2205/12* (2013.01); *A61M 2209/088* (2013.01); *A61M 2210/04* (2013.01)

(58) Field of Classification Search
CPC ......... A61M 2005/14256; A61M 2005/14533; A61M 2005/1585
See application file for complete search history.

(56) References Cited

U.S. PATENT DOCUMENTS 8,382,700 B2 2/2013 Straessler et al.
8,957,674 B2 2/2015 Genoud et al.
9,222,470 B2 12/2015 Genoud et al.
9,302,285 B2 4/2016 Marbet et al.
9,610,402 B2 * 4/2017 Yavorsky .............. A61M 5/142
9,662,621 B2 5/2017 Beyer et al.
10,076,605 B2 9/2018 Marbet et al.
10,143,798 B2 12/2018 Marbet et al.
10,569,011 B2 * 2/2020 Dilanni ............. A61M 5/14566
10,632,249 B2 4/2020 Marbet et al.
10,954,928 B2 3/2021 Burli et al.
11,009,018 B2 5/2021 Wyss et al.
11,009,026 B2 5/2021 Girschweiler et al.
11,022,107 B2 6/2021 Brandt et al.
11,160,922 B2 11/2021 Just
11,612,687 B2 3/2023 Marbet
11,744,940 B2 9/2023 Wieser et al.
2002/0055711 A1 * 5/2002 Lavi ...................... A61M 5/326 604/110
2008/0208139 A1 * 8/2008 Scheurer ............... A61M 5/158 604/192
2009/0030382 A1 1/2009 Brandt et al.
2010/0241063 A1 9/2010 Straessler et al.
2012/0046651 A1 2/2012 Beyer et al.
2014/0231549 A1 8/2014 Thiemer et al.
2016/0184512 A1 * 6/2016 Marbet ............. A61M 5/14248 604/157
2016/0199590 A1 * 7/2016 Schabbach .............. A61M 5/34 604/240
2016/0213837 A1 7/2016 Schabbach et al.
2016/0213839 A1 7/2016 Schabbach et al.
2016/0339179 A1 * 11/2016 Lemaire .................. A61M 5/46
2019/0117880 A1 * 4/2019 Hirschel ........... A61M 5/31576
2019/0160225 A1 * 5/2019 Verlaak ............. A61M 5/14248
2020/0023122 A1 * 1/2020 McCullough ..... A61M 5/14248
2021/0369957 A1 * 12/2021 Wieser .................. A61M 5/321
2022/0031940 A1 2/2022 Hulliger et al.
2022/0226567 A1 * 7/2022 Pananen ............. A61M 5/3287
2023/0398289 A1 12/2023 Wieser et al.
2024/0033422 A1 2/2024 Büchi et al.
2024/0033423 A1 2/2024 Muller et al.
2024/0066541 A1 2/2024 Perrier et al.
2024/0082485 A1 3/2024 Lagorgette et al.
2024/0082486 A1 3/2024 Lagorgette et al.
2024/0091460 A1 3/2024 Burli et al.
2024/0157045 A1 5/2024 Kostal et al.
2024/0165325 A1 5/2024 Burli
2024/0173473 A1 5/2024 Burli
2024/0175431 A1 5/2024 Mueller
2024/0181153 A1 6/2024 Kostal et al.

FOREIGN PATENT DOCUMENTS

WO WO 2008/065646 6/2008
WO WO-2008065646 A1 * 6/2008 ......... A61B 5/14503
WO WO 2015/015379 2/2015
WO WO 2018/024625 2/2018
WO WO 2018/060027 4/2018
WO WO 2019/228895 12/2019
WO WO 2020/069926 4/2020
WO WO 2022/194611 9/2022

* cited by examiner 1
2
3
4
5
40
46
48
50
51

56
20
9
22
48a
28
10
62
27
38
29
31
18
14
12
13
33

16b
16a
14
12
27
28
56
48a
10
16
7
40
18
21
19
25
23
6
11
13
9
30
26b
26a
26c
B 12
26c
28
10

12
26c
28
10

16a
7
40
16b
21
23
18
19
26a
28
B
9
B
13
48a
25
26b
26c
14

7
18
26c
26a
28
13 B
B
14
30
9
26b
10

DRUG DELIVERY DEVICE

TECHNICAL FIELD

This invention relates to a drug delivery device for subcutaneous administration of a liquid drug. The invention in particular relates to a drug delivery device in the form of a patch device.

DESCRIPTION OF RELATED ART

Drug delivery devices in the form of a patch device for mounting on a patient's skin for subcutaneous delivery of liquid drug are known. It is known to provide drug delivery devices in the form of a patch device with a single use disposable component assembled to a reusable component containing drive and control electronics, or as a single disposable component.

The reliability, safety, compactness and ease of use of drug delivery devices worn by a patient is important. For disposable components, the amount of parts and consequently cost of the disposable device is also an important consideration.

For safety of use of the drug delivery device, it is also important to ensure that it may only be actuated when attached to a patient's skin, that it remains sterile until administration of the drug, and that after use and removal the disposable portion of the device cannot be reused or harm someone.

In known drug delivery devices provided as patch devices that are placed against a patient's skin and held by an adhesive, an injection needle is actuated upon activation of the device for the sub-cutaneous delivery of the liquid medication. After use, the injection needle is retracted into the drug delivery device to avoid injury after removal of the patch device from the patient's skin. In certain patch devices, the needle is used to insert a soft cannula and thus performs an insertion and retraction movement prior to pumping of the liquid medication, and in certain patch devices a hollow rigid needle is inserted and remains in an extended position for sub-cutaneous drug delivery and retracts at the end of the drug delivery prior to removal of the patch device from the patient's skin. In the case of delivery devices with rigid needles (instead of soft cannulas) which have less complex mechanisms than devices with soft cannulas, a drawback is that the retraction at the end of the drug delivery cycle requires power and if there is a failure of the device or a loss of power it is possible that the needle remains in an extended position. Moreover, in many devices a retraction mechanism requires a somewhat complex arrangement, in particular to ensure that once retracted the needle remains in the retracted position.

There is need to ensure safety and reliability of mechanisms operated automatically in a drug delivery device, while decreasing costs and increasing the compacity of the medical device.

SUMMARY OF THE INVENTION

In view of the foregoing, it is an object of the invention to provide a drug delivery device, in particular in the form of a patch device, with a disposable unit, or as an entirely disposable device, for administration of a liquid drug that is safe, reliable, and compact.

It is advantageous to provide a drug delivery device that is easy to use.

It is advantageous to provide a drug delivery device that is economical to produce.

Objects of the invention have been achieved by providing the drug delivery device as described herein. Dependent claims set forth various advantageous embodiments of the invention.

Objects of this invention have been achieved by providing a system as described herein. Dependent claims set forth various advantageous features of embodiments of the invention.

Disclosed herein is a drug delivery device, including a delivery unit comprising a subcutaneous delivery system including a needle support, an injection needle mounted on the needle support, and an injection needle actuation mechanism configured to engage and slidably move the needle support from a retracted position where the injection needle is within a housing of the drug delivery device to an extended delivery position where the injection needle projects through a skin contact wall of the housing. The needle actuation mechanism comprises a slider-crank linkage mechanism comprising a crank rod pivotally connected to the housing, a connecting rod pivotally connected to the crank rod and pivotally connected to the slidable needle support, and a spring biasing the slider-crank linkage mechanism from a first retracted position prior to use where the needle is fully inserted within the housing towards an extended position for drug administration and further to a second retracted position after use.

In an advantageous embodiment, the spring is a torsion spring having a first arm engaging a support structure of the housing and a second arm engaging the slider-crank linkage mechanism.

In a variant, the spring is a tension or compression spring engaging a support structure of the housing and a second arm engaging the crank rod or connecting rod of the slider-crank linkage mechanism.

In an advantageous embodiment, the needle actuation mechanism further comprises a rotatable actuation disc having a radial cam including a blocking portion configured to hold the slider-crank linkage mechanism in the first retracted position, and a release portion configured to allow the slider-crank linkage mechanism to move.

In an advantageous embodiment, the actuation disc is coupled to a pumping system of the drug delivery device.

In an advantageous embodiment, the actuation disc is coupled to a rotor of a pump engine of the pumping system.

In an advantageous embodiment, the drug delivery device further comprises an actuation lock comprising a blocking pad engaging the radial cam on one side of the blocking pad and the crank rod or connecting rod on the other side of the blocking pad.

In an advantageous embodiment, the actuation lock is pivotally mounted to the support structure, the actuation lock comprising an arm extending from a pivot coupling to the blocking pad.

In an advantageous embodiment, the actuation lock comprises a disengagement finger configured to be engaged by the slidable needle support in the extended position such that the blocking pad is moved away from the radial cam.

In an advantageous embodiment, the drug delivery device further comprises a stopper configured to stop the slideable needle support or slider-crank linkage mechanism in the extended position for drug administration, the stopper configured to be displaced to release the slider-crank linkage mechanism after use and removal of the drug delivery device.

The moveable stopper may be flexibly, elastically, slidably or pivotally coupled to the housing.

In an advantageous embodiment, the stopper is pivotally coupled to the housing via a pivot coupling.

In an advantageous embodiment, the stopper forms a skin contact wall portion configured to be in abutment against the skin of the patient during drug administration.

In an advantageous embodiment, the skin contact wall portion comprises the needle orifice formed therethrough.

BRIEF DESCRIPTION OF THE DRAWINGS

Further objects and advantageous features of the invention will be apparent from the claims, from the detailed description, and annexed drawings, in which:

DETAILED DESCRIPTION OF EXEMPLARY EMBODIMENTS

Figures 1A, 1B:
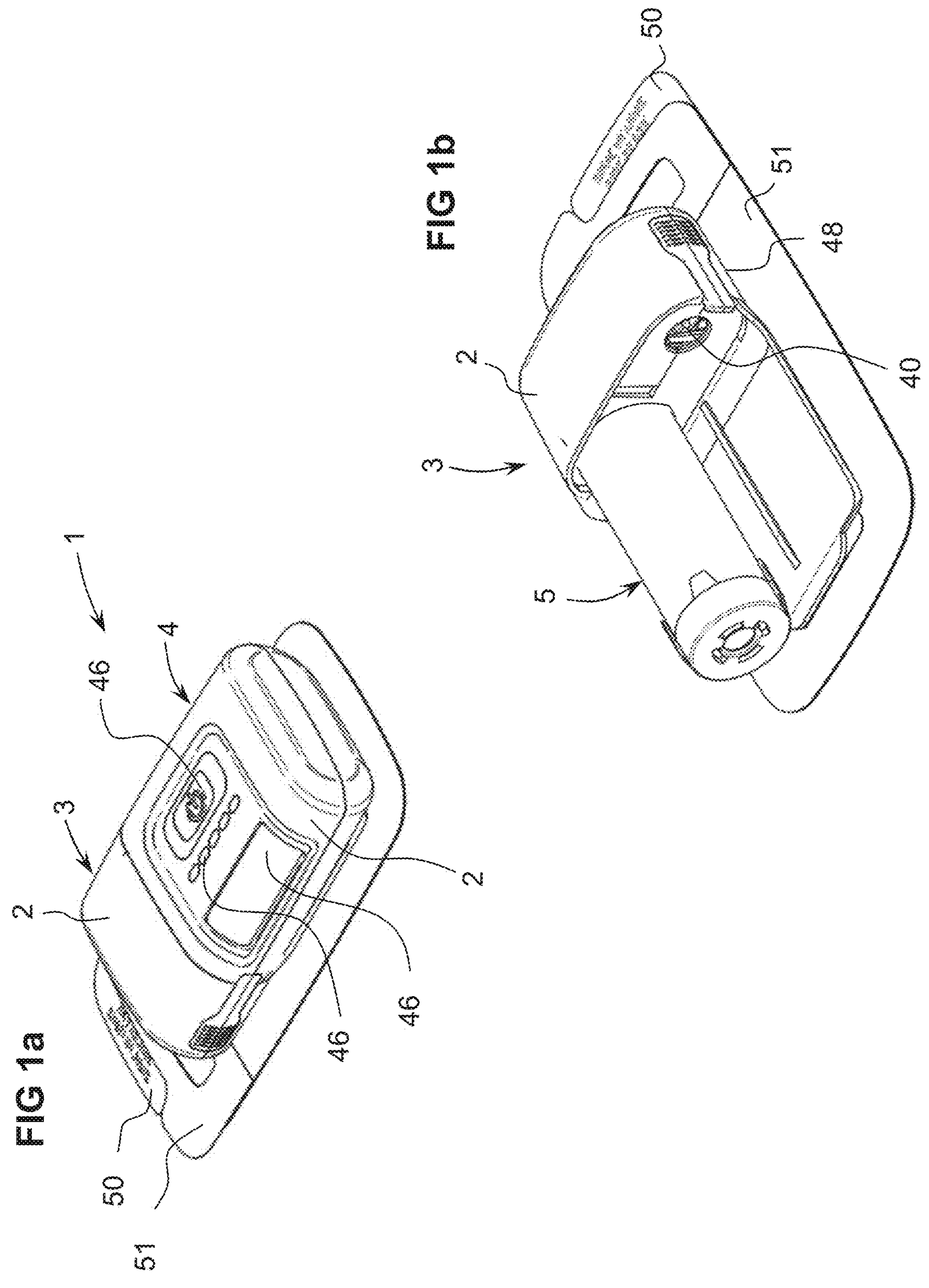
FIG. 1*a* is a perspective view of a drug delivery device according to an embodiment of the invention.
FIG. 1*b* is a perspective view of a disposable unit of the drug delivery device of FIG. 1*a;*
Figure 2:
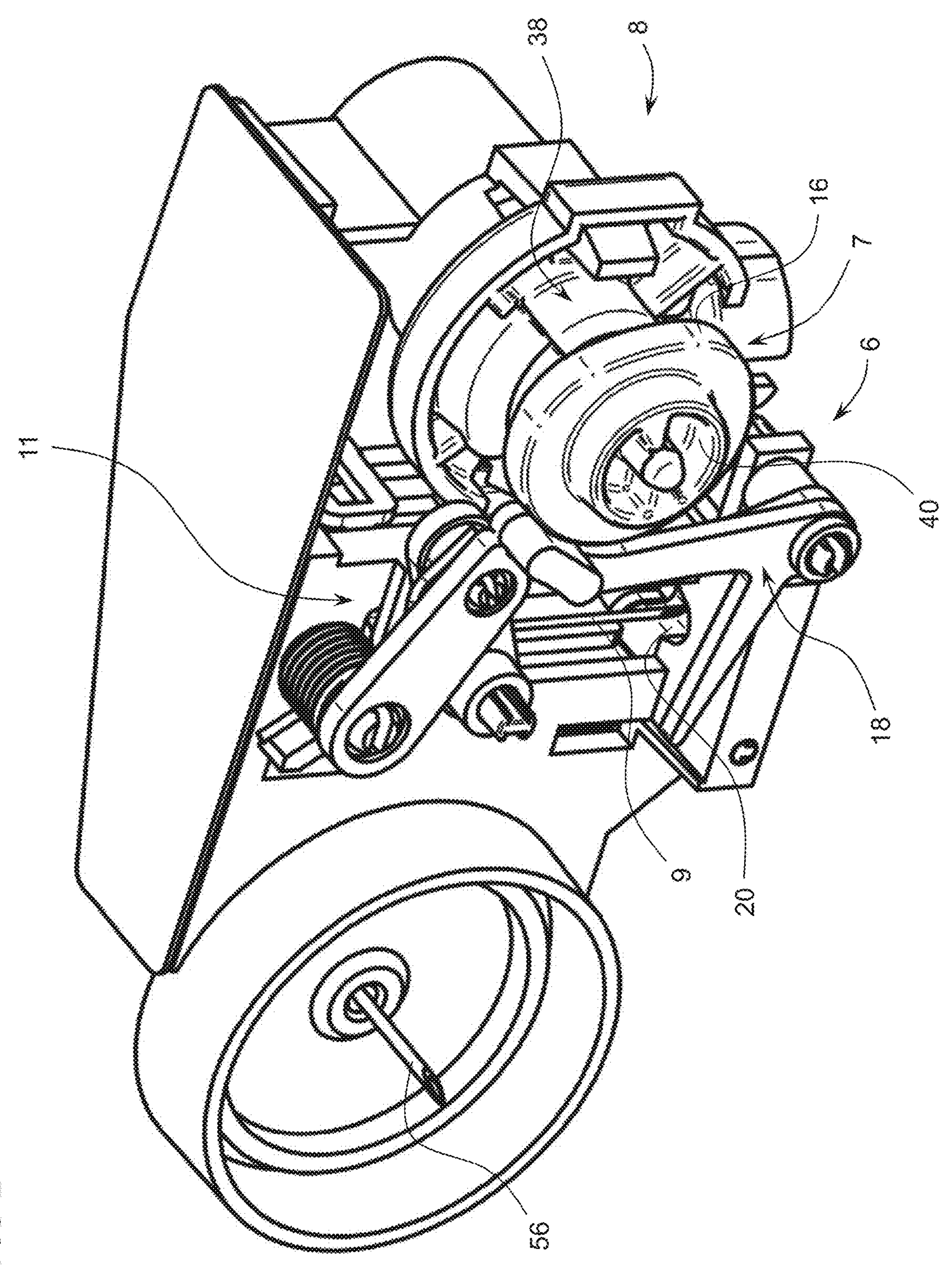
FIG. 2 is a perspective view of an inner portion of the delivery unit of FIG. 1*b* with a housing removed to illustrate a needle actuation mechanism according to an embodiment of the invention.

Referring to the figures, a drug delivery device 1 according to embodiments of the invention comprises a housing 2, a delivery unit 3, and a control or drive unit 4, the delivery unit 3 and the control or drive unit 4 being assembled within the housing 2. The housing 2 may be made of two or more parts allowing assembly of the delivery unit, drive unit and any other components within the housing.

In the illustrated embodiments, the drug delivery device for subcutaneous administration of a liquid drug (medicament) comprises a disposable portion formed by the delivery unit that may be assembled to a reusable portion formed by the drive unit, which includes electronics and a power supply. The delivery unit 3 is mounted in a first housing portion of the drug delivery device and the drive unit 4 in a separable second housing portion such that the drive unit 4 can be reused with subsequent delivery units.

Although the embodiments shown in the figures concern a two-part drug delivery device with disposable and reusable units, within the scope of the invention for various aspects described herein, the drug delivery device may be a single use disposable unit. The administration may occur in a single dose over a short period of time, typically less than 1 hour, for instance around 30 minutes or less. A single use disposable drug delivery device may also be used for subcutaneous injection of a liquid drug over an extended period of time from a few hours to a few days.

The drug delivery device includes a user interface 46 that may include one or more buttons for actuating the drug delivery device, light and/or sound status indicators, and optionally a screen or other display for presenting information to an operator of the device.

Drug delivery devices according to embodiments of the invention may advantageously be configured as a patch device for mounting on a patient's skin.

Referring to FIGS. 1*a* and 1*b*, an adhesive layer 51 may be provided on an outer surface of a skin contact wall 48 of the housing 2 covered by a protective film 50 that may be peeled off the adhesive layer 51 prior to placing the adhesive layer on the patient's skin at the site of injection. A needle orifice 20 on the skin contact side is covered by the protective film 50 prior to use, and allows a transcutaneous injection needle 9 to extend therethrough and pierce the patient's skin upon activation of the drug delivery device 1.

The delivery unit 3 comprises a drug container 5, for instance a drug cartridge, containing a liquid drug and a liquid flow system for channeling the liquid drug to a patient subcutaneously.

The drug delivery device further includes a pumping system that causes liquid from the drug container to be pumped to the injection needle 9 once the drug delivery device has been activated.

In an embodiment, the delivery unit 3 incorporates a pump engine 38 of the pumping system 8 that causes liquid from the container to be pumped to the injection needle 9 once the drug delivery device has been activated. The pump engine 38 comprises a drive coupling interface 40 that couples to a complementary coupling interface of a pump drive of the drive unit 4. The drive unit thus provides the mechanical power via the coupling interface 40 to drive the pump engine 38.

The pump engine 38 in the delivery unit 3 may advantageously comprise a design and configuration similar to the pump engine described in WO 2007074363, WO 2015015379, WO2019228895A1, or WO2020069926A1, in which a rotor 31 is mounted within a stator 29 and is rotatably and axially movable within the stator 29 in order to pump a fluid from a fluid inlet to a fluid outlet. As known from the above-mentioned publications, the rotor 31 has a pump shaft with first and second diameters surrounded by seals that open and close a fluid channel between the inlet and outlet as the rotor rotates and axially displaces due to a cam mechanism between the stator 29 and rotor 31, whereby during the opening and closing of the valves between the fluid inlet and pumping chamber, respectively between the pumping chamber and outlet, a pumping action is performed.

An important advantage of using such pump engine in embodiments of the present drug delivery device is that there is no direct connection of fluid between the inlet and outlet at any position of the rotor and no actuation of any valves are required, such that a particularly reliable pumping of liquid without leakage is ensured in an easy to operate arrangement. The pump engine is very compact and can be driven directly by a rotary electrical motor of the pump drive in the drive unit 4 without gearing. In effect, because of the differential pumping volume displacement that is defined by the axial displacement of the rotor and the difference between the first and second diameters of the pump shaft, the pumping volume displacement rotation can be easily configured for optimal operation with an electrical motor of a given type rotating with a constant speed. Moreover, the pump engine parts can be made entirely of polymer materials and the rotor may be easily coupled to the pump drive ensuring a sterile barrier between the fluidic portion of the pump engine and the coupling interface.

In other embodiments, the pumping system may be mounted in the drive unit and apply pressure on a plunger of the drug container to push liquid out of the drug container into the subcutaneous delivery system by positive pressure. Various per se known means for applying pressure on a drug container plunger may be employed.

In another specific embodiment, the pumping system may comprise a pneumatic pumping system as described in patent application PCT/EP2022/055835.

The pumping system may also include other per se well known pumping systems, for instance the motor may drive a linear nut and screw system that presses on the plunger.

The drive unit 4 is configured principally to drive the pumping system, but may also have additional functions such as processing sensing signals, and transmitting and receiving data from an external device via a wireless communication link, for instance using Bluetooth.

Figures 4A, 4B, 5A, 5B:
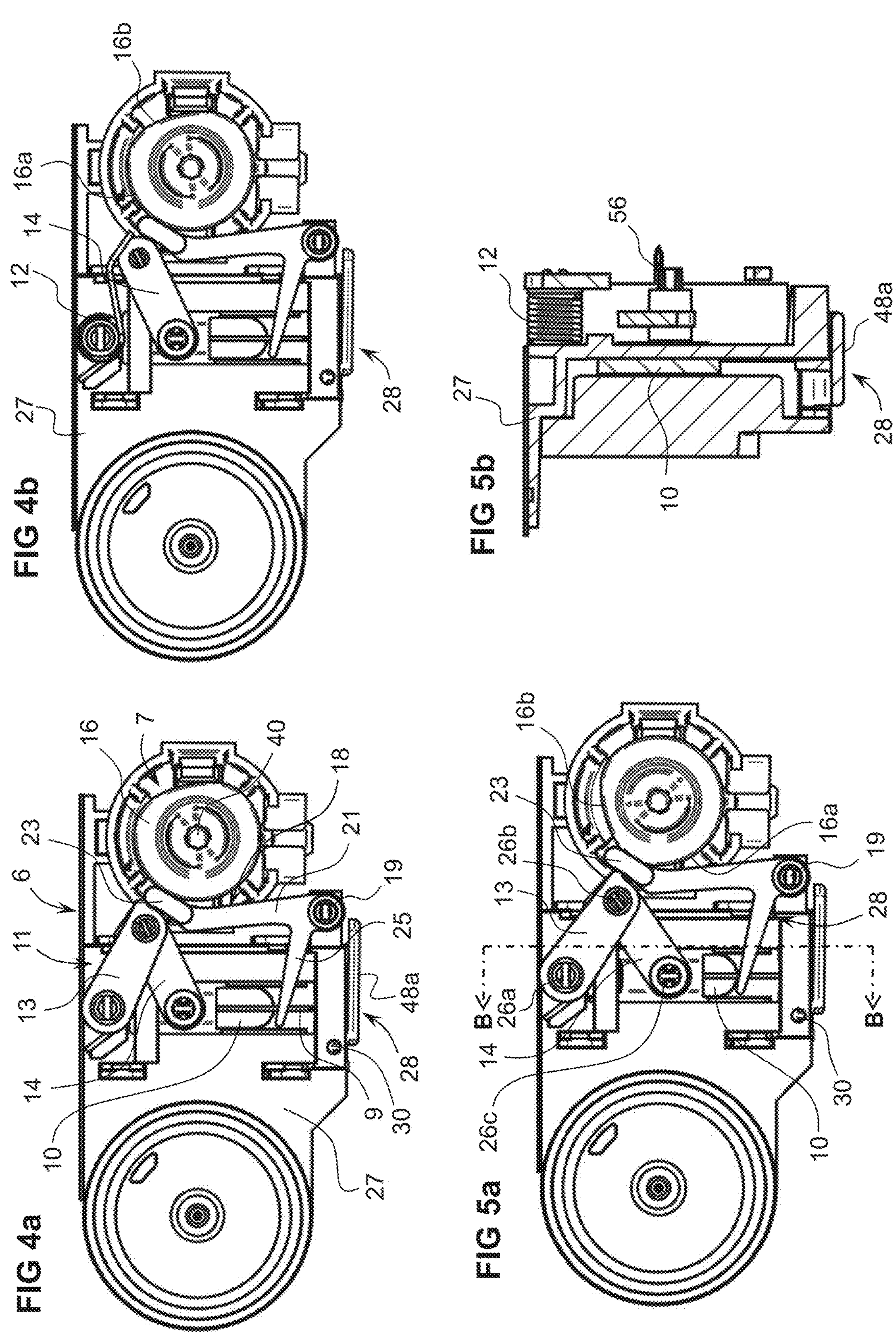
FIG. 4*a* is a plan view of the inner portion shown in FIG. 2, showing the needle actuation mechanism in an initial state prior to use.
FIG. 4*b* is a view similar to FIG. 4*a* with a crank rod of the needle actuation mechanism removed to better see a spring and connecting rod of the needle actuation mechanism.
FIG. 5*a* is a view similar to FIG. 4*a* showing an initial phase in the actuation of the drug delivery device.
FIG. 5*b* is a cross-sectional view through line B-B of FIG. 5*a;*
Figures 6A, 6B, 7A, 7B:
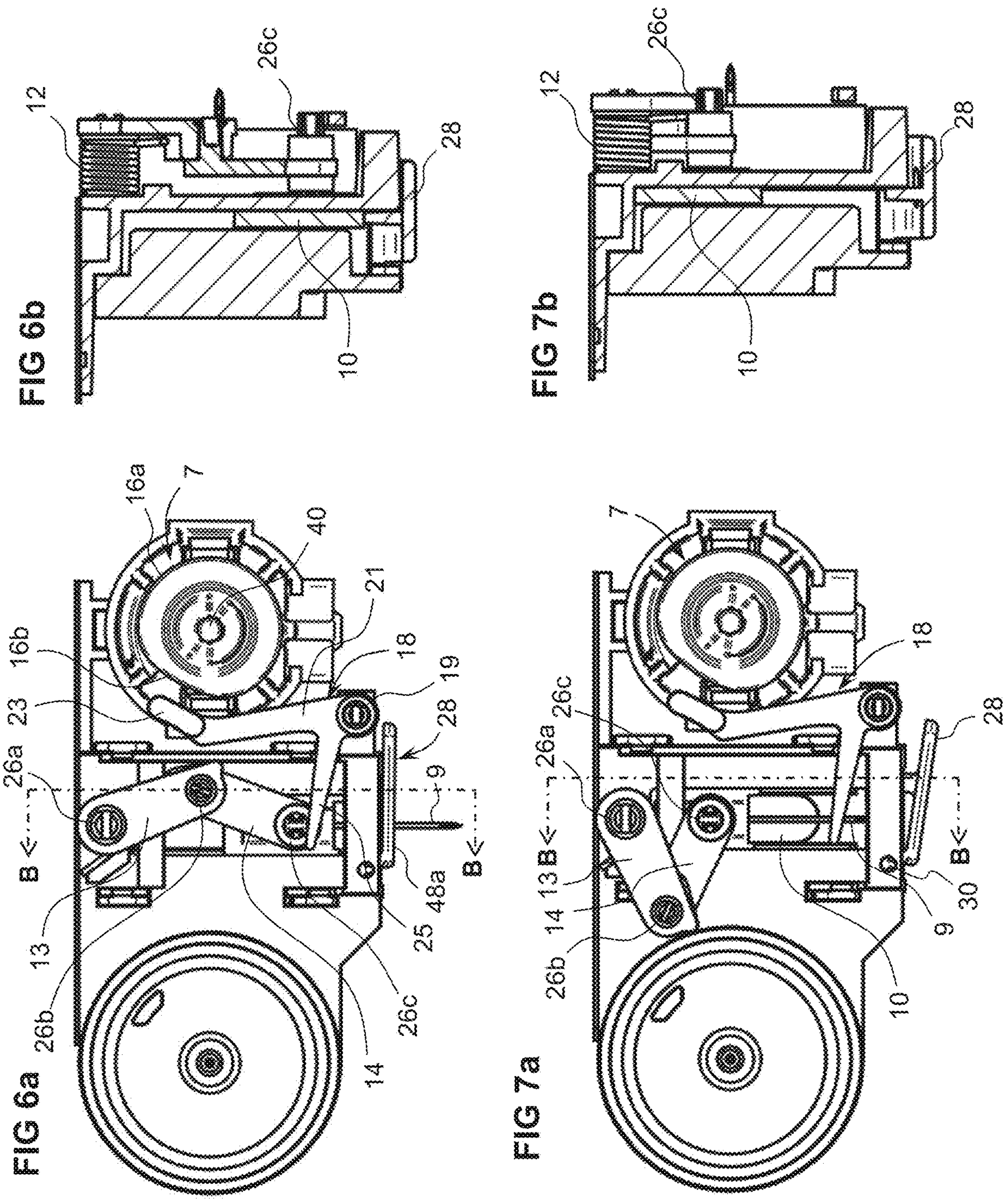
FIG. 6*a* is a view similar to FIG. 5*a* showing a subsequent delivery phase of the drug delivery device with the injection needle in a fully extended delivery position.
FIG. 6*b* is a cross-sectional view through line B-B of FIG. 6*a;*
FIG. 7*a* is a view similar to FIG. 6*a* showing a final phase in the actuation of the drug delivery device with the needle in a retracted position after removal of the drug delivery device from a patient.
FIG. 7*b* is a cross-sectional view through line B-B of FIG. 7*a*.

The subcutaneous delivery system comprises a slidable needle support 10 which is slidably mounted within the housing 2, the needle 9 being mounted on the needle support 10 and movable with the needle support 10 from a fully retracted position within the housing 2 of the delivery unit 3 as illustrated in FIG. 4*a*, to a fully extended position during drug administration as illustrated in FIG. 6*a*.

Figure 3:
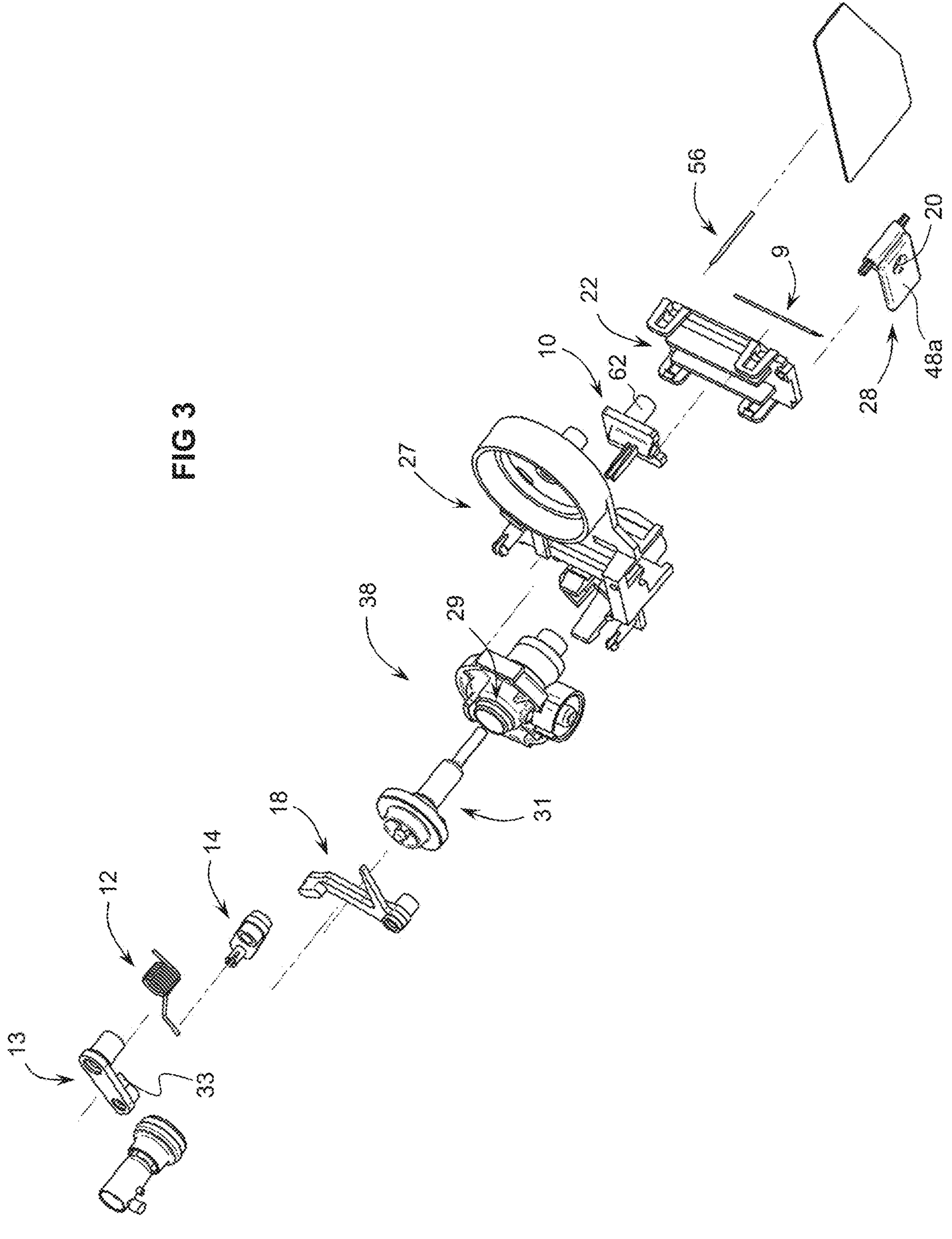
FIG. 3 is an exploded perspective view of the inner portion shown in FIG. 2.

A fluidic channel within the needle support is connected fluidically to the fluid channel in the needle and to a conduit (not illustrated) that may advantageously be in the form of a supple tube coupled to an inlet 62 of the fluidic channel (see FIG. 3) allowing the sliding movement of the needle support from the retracted position to the extended position. The tube is connected fluidically at its other end to a drug container, for instance to the drug container in the form of a drug cartridge via a septum needle 56 that pierces through the septum of the drug container 5.

In variants, other fluidic connections and drug containers may be provided, for instance the tube may be connected to a drug container of another configuration, for instance a supple container, or a container directly formed in the drug delivery device (instead of being provided as a separate cartridge).

The needle actuation mechanism 6 comprises a slider-crank linkage mechanism 11 that is configured to move the slidable needle support 10 from a retracted position where the needle is fully retracted within the housing prior to administration of the drug, to an extended position where the needle pierces through the patient's skin for administration of the liquid drug. The slider-crank linkage mechanism 11 is further configured to move the slidable needle support 10 back to a retracted position where the needle is fully within the housing, after use and removal of the drug delivery device from a patient's skin.

The slider-crank linkage mechanism 11 comprises a spring 12, a crank rod 13 coupled pivotally via a first pivot coupling 26*a* to a support structure 27 statically assembled to or forming part of the housing 2, and a connecting rod 14 coupled pivotally to the crank rod via a second pivot coupling 26*b* and further coupled pivotally to the slidable needle support via a third pivot coupling 26*c*. The spring is configured to apply a spring force on the crank rod 13 to rotate it one rotational direction from a first retracted position to the extended position and then to a second retracted position.

In the illustrated example the spring 12 is in the form of a torsion spring having one arm connected to the support structure 27 and the other arm engaging a spring catch shoulder 33 provided on the crank rod 13.

In variants, the spring could however be a traction spring or compression spring that for instance is attached at one end to the support structure 27 and at the other end to the crank rod or connecting rod at or proximate the second pivot coupling 26*b*, thereby applying a traction or pushing force seeking to rotate the crank rod in one direction.

In the illustrated example, the crank rod 13 rotates from the first retracted position to the second retracted position through an angle of less than 180 degrees, in a range of 120 to 180 degrees.

In the extended position for drug administration as illustrated in FIGS. 6*a* and 6*b*, the crank rod and connecting rod are in a position that slightly precedes the bottom dead centre position of the slidable needle support 10, for instance by an angle of the connecting rod within a range of 5 to 15 degrees from the bottom dead centre position. The slidable needle support 10 is stopped from further sliding towards its bottom dead centre position by a stopper 28.

In the illustrated embodiment, the stopper 28 is in the form of a moveable wall comprising a skin contact wall portion 48*a* that is configured to be in contact with the patient's skin during drug administration. The skin contact wall portion 48*a* of the stopper may further include the needle orifice 20. When the drug delivery device is removed from the patient and the stopper 28 is no longer pressed against the patient's skin, the slider-crank linkage mechanism 11 under the biasing force of the spring 12 displaces the stopper away from its position during drug administration such that the crank rod and connecting rod can continue to rotate and move the slidable needle support 10 back to a retracted position as shown in FIGS. 7*a* and 7*b*.

The slider-crank linkage mechanism 11 is thus held in the extended position for drug administration as illustrated in FIGS. 6*a* and 6*b* by abutment of the slidable needle support against the stopper 28, and upon release of the stopper 28 when the drug delivery device is removed from the patient, the crank rod and connecting rod can continue their rotation to the second retracted position.

In the illustrated example, the stopper is rotatable and coupled via a pivot coupling 30 to the housing 2. In variants, the stopper may however be slidably coupled to the housing instead of pivotally coupled. The stopper may in variants also be coupled to the housing via an elastic or flexible coupling, for instance an integrally formed flexible web forming for instance a hinge coupling the stopper to the housing or an extendable joint allowing the stopper to flexibly translate downwards relative to the housing.

The needle actuation mechanism further comprises an actuation lock device 18 that blocks the slider-crank linkage mechanism and slidable needle support 10 in the first retracted position prior to use, for instance as illustrated in FIGS. 4*a* and 4*b*.

The actuation lock device 18 is held in the position prior to use by an actuation disc 7 having a radial cam 16 against which the actuation lock is pressed by the slider-crank linkage mechanism 11 due to the rotational force on the crank rod 13 by the spring 12. The cam 16 has a blocking portion 16*a* and a release portion 16*b* with a smaller radius than the blocking portion 16*a*. The release portion is configured to allow the actuation lock 18 to bias away from the slider-crank linkage mechanism 11 to an extent sufficient to allow the crank rod and connecting rod to rotate to the extended position for drug delivery.

The actuation disc 7 is coupled to a motor drive (not shown) that rotates the actuation disc when the drug delivery device commences the process for drug administration. The actuation disc 7 may advantageously be coupled to the pumping system 8 such that pumping of the liquid drug for drug administration occurs necessarily after the needle has been actuated into the extended position for drug administration. In variants, the actuation disc may however be driven by a motor or mechanism independently of the pumping system.

In a variant, it is possible to omit the actuation lock 18 and have the blocking portion 16*a* or the cam 16 of the actuation disc 7 directly engage the crank rod 13 or connecting rod 14 of the slider-crank linkage mechanism, for instance at a position proximate the second pivot coupling 26*b* between the connecting rod and crank rod. Upon rotation of the actuation disc 7, the release portion 16*b* of the cam which is at a smaller radius that the blocking portion 16*b* disengages from the crank rod and connecting rod such that the slider-crank linkage mechanism can freely rotate to the extended position for drug delivery.

In the illustrated embodiment, the actuation lock 18 comprises an arm 21 coupled to the housing via a pivot coupling 19, a free end of the arm 21 having a blocking pad 23 that engages on one side the cam 16 and on the other side the slider-crank linkage mechanism 11.

The actuation lock 18 may further comprise a disengagement finger 25 that is engaged by the slider-crank linkage mechanism 11 or slidable needle support 10 at the extended position for drug administration to move the blocking pad 23 away from the cam 16 such that there is no contact between the actuation disc and actuation lock 18 during subsequent rotation of the actuation disc. This is useful in embodiments where the actuation disc is coupled to the pumping system.

LIST OF REFERENCES USED

Drug delivery device 1
Housing 2
Skin contact wall 48
Needle orifice 20
skin contact wall portion 48*a*
Adhesive layer 51
Protective film 50
Support structure 27
Delivery unit 3
Drug container 5
Subcutaneous delivery system
Injection needle 9
Slideable needle support 10
Fluidic channel inlet 62
Housing slide 22
Septum needle 56
Needle actuation mechanism 6
Actuation disc 7
Cam 16
Blocking portion 16*a*
Release portion 16*b*
Actuation lock 18
Pivot coupling 19
Arm 21
Blocking pad 23
Disengagement finger 25
Slider-crank linkage mechanism 11
Torsion spring 12
Crank rod 13
Spring catch shoulder 33
Connecting rod 14
Slideable needle support 10
Pivot couplings 26*a*, 26*b*, 26*c*
Stopper 28
Pivot coupling 30
Needle orifice 20
Skin contact wall portion 48*a*
Pumping system 8
Pump engine 38
Stator 29
Rotor 31
Drive coupling interface 40
Drive unit 4
Electronic control system
Power source (battery)
Pump drive
Motor
Coupling interface
User interface 46

The invention claimed is:

1. A drug delivery device, including a delivery unit comprising a subcutaneous delivery system including a slidable needle support, an injection needle mounted on the slidable needle support, and an injection needle actuation mechanism configured to engage and slidably move the slidable needle support from a retracted position where the injection needle is within a housing of the drug delivery device to an extended delivery position where the injection needle projects through a skin contact wall of the housing, wherein the needle actuation mechanism comprises a slider-crank linkage mechanism comprising a crank rod pivotally connected to the housing, a connecting rod pivotally connected to the crank rod and pivotally connected to the slidable needle support, and a spring biasing the slider-crank linkage mechanism from a first retracted position prior to use where the needle is fully inserted within the housing towards an extended position for drug administration and further to a second retracted position after drug administration, wherein the needle actuation mechanism further comprises a rotatable actuation disc having a radial cam including a blocking portion configured to hold the slider-crank linkage mechanism in the first retracted position, and a release portion configured to allow the slider-crank linkage mechanism to move.

2. The drug delivery device of claim 1, wherein the spring is a torsion spring having a first arm engaging a support structure of the housing and a second arm engaging the slider-crank linkage mechanism, wherein the support structure is statically assembled to the housing or forms part of the housing.

3. The drug delivery device of claim 1, wherein the spring is a tension or compression spring having a first end engaging a support structure of the housing and a second end engaging the crank rod or connecting rod of the slider-crank linkage mechanism, wherein the support structure is statically assembled to the housing or forms part of the housing.

4. The drug delivery device of claim 1, wherein the actuation disc is coupled to a pumping system of the drug delivery device.

5. The drug delivery device of claim 1, wherein the actuation disc is coupled to a rotor of a pump engine of the pumping system.

6. The drug delivery device of claim 1, further comprising a stopper configured to stop the slideable needle support or slider-crank linkage mechanism in the extended position for drug administration, the stopper configured to be displaced to release the slider-crank linkage mechanism after use and removal of the drug delivery device.

7. The drug delivery device of claim 6, wherein the stopper is flexibly, elastically, slidably or pivotally coupled to the housing.

8. The drug delivery device of claim 6, wherein the stopper is pivotally coupled to the housing via a pivot coupling.

9. The drug delivery device of claim 6, wherein the stopper forms a skin contact wall portion configured to be in abutment against the skin of the patient during drug administration.

10. A drug delivery device, including a delivery unit comprising a subcutaneous delivery system including a slidable needle support, an injection needle mounted on the slidable needle support, and an injection needle actuation mechanism configured to engage and slidably move the slidable needle support from a retracted position where the injection needle is within a housing of the drug delivery device to an extended delivery position where the injection needle projects through a skin contact wall of the housing, wherein the needle actuation mechanism comprises a slider-crank linkage mechanism comprising a crank rod pivotally connected to the housing, a connecting rod pivotally connected to the crank rod and pivotally connected to the slidable needle support, and a spring biasing the slider-crank linkage mechanism from a first retracted position prior to use where the needle is fully inserted within the housing towards an extended position for drug administration and further to a second retracted position after drug administration, further comprising an actuation lock comprising a blocking pad engaging a radial cam on one side of the blocking pad and the crank rod or connecting rod on the other side of the blocking pad.

11. The drug delivery device of claim 10, wherein the actuation lock is pivotally mounted to the support structure, the actuation lock comprising an arm extending from a pivot coupling to the blocking pad.

12. The drug delivery device of claim 10, wherein the actuation lock comprises a disengagement finger configured to be engaged by the slidable needle support in the extended position such that the blocking pad is moved away from the radial cam.

13. The drug delivery device of claim 10, wherein the spring is a torsion spring having a first arm engaging a support structure of the housing and a second arm engaging the slider-crank linkage mechanism, wherein the support structure is statically assembled to the housing or forms part of the housing.

14. The drug delivery device of claim 10, wherein the spring is a tension or compression spring having a first end engaging a support structure of the housing and a second end engaging the crank rod or connecting rod of the slider-crank linkage mechanism, wherein the support structure is statically assembled to the housing or forms part of the housing.

15. The drug delivery device of claim 10, wherein the needle actuation mechanism further comprises a rotatable actuation disc having a radial cam including a blocking portion configured to hold the slider-crank linkage mechanism in the first retracted position, and a release portion configured to allow the slider-crank linkage mechanism to move.

16. The drug delivery device of claim 15, wherein the actuation disc is coupled to a pumping system of the drug delivery device.

17. The drug delivery device of claim 15, wherein the actuation disc is coupled to a rotor of a pump engine of the pumping system.

18. The drug delivery device of claim 10, further comprising a stopper configured to stop the slideable needle support or slider-crank linkage mechanism in the extended position for drug administration, the stopper configured to be displaced to release the slider-crank linkage mechanism after use and removal of the drug delivery device.

19. A drug delivery device, including a delivery unit comprising a subcutaneous delivery system including a slidable needle support, an injection needle mounted on the slidable needle support, and an injection needle actuation mechanism configured to engage and slidably move the slidable needle support from a retracted position where the injection needle is within a housing of the drug delivery device to an extended delivery position where the injection needle projects through a skin contact wall of the housing, wherein the needle actuation mechanism comprises a slider-crank linkage mechanism comprising a crank rod pivotally connected to the housing, a connecting rod pivotally connected to the crank rod and pivotally connected to the slidable needle support, and a spring biasing the slider-crank linkage mechanism from a first retracted position prior to use where the needle is fully inserted within the housing towards an extended position for drug administration and further to a second retracted position after drug administration, further comprising a stopper configured to stop the slideable needle support or slider-crank linkage mechanism in the extended position for drug administration, the stopper configured to be displaced to release the slider-crank linkage mechanism after use and removal of the drug delivery device, wherein the stopper forms a skin contact wall portion configured to be in abutment against the skin of the patient during drug administration, wherein the skin contact wall portion comprises a needle orifice formed therethrough configured to allow the injection needle to pass therethrough between the extended and retracted positions.

* * * * *